(12) United States Patent
Kveen et al.

(10) Patent No.: US 7,740,654 B2
(45) Date of Patent: *Jun. 22, 2010

(54) HELICAL STENT DESIGN

(75) Inventors: Graig L. Kveen, Maple Grove, MN (US); Burns P. Doran, Albertville, MN (US); Robert T. Judnitch, Crystal, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 676 days.

This patent is subject to a terminal disclaimer.

(21) Appl. No.: 11/137,461

(22) Filed: May 25, 2005

(65) Prior Publication Data

US 2005/0216076 A1   Sep. 29, 2005

Related U.S. Application Data

(63) Continuation of application No. 10/280,960, filed on Oct. 25, 2002, now Pat. No. 6,949,120, which is a continuation of application No. 09/537,244, filed on Mar. 28, 2000, now Pat. No. 6,488,703, which is a continuation of application No. 09/178,457, filed on Oct. 23, 1998, now Pat. No. 6,042,597.

(51) Int. Cl.
A61F 2/06 (2006.01)
(52) U.S. Cl. .................................................. 623/1.15
(58) Field of Classification Search ................ 623/1.15, 623/1.16, 1.12, 1.17, 1.2; 606/191, 195, 606/198
See application file for complete search history.

(56) References Cited

U.S. PATENT DOCUMENTS

| 4,886,062 A | 12/1989 | Wiktor |
| 5,135,536 A | 8/1992 | Hillstead |
| 5,139,480 A | 8/1992 | Hickle et al. |
| 5,226,913 A | 7/1993 | Pinchuk |
| 5,344,426 A | 9/1994 | Lau et al. |
| 5,370,683 A | 12/1994 | Fontaine |
| 5,443,498 A | 8/1995 | Fontaine |
| 5,449,373 A * | 9/1995 | Pinchasik et al. ............ 606/198 |
| 5,496,365 A | 3/1996 | Sgro |
| 5,536,274 A | 7/1996 | Neuss |

(Continued)

FOREIGN PATENT DOCUMENTS

EP    0 565 251 A1    10/1993

(Continued)

OTHER PUBLICATIONS

U.S. Appl. No. 10/280,960, filed Oct. 25, 2002, Kveen et al.

(Continued)

*Primary Examiner*—Kevin T Truong
(74) *Attorney, Agent, or Firm*—Vidas, Arrett & Steinkraus P.A.

(57) ABSTRACT

An expandable tubular reinforcing member used for body lumens such as blood vessels, the reinforcing member being formed of a continuous elongated helical element comprised of spaced undulating portions forming end loop portions and including a plurality of curvilinear connector elements extending between and interconnecting at least some of the adjacent undulating portions of the helical element over its length.

21 Claims, 8 Drawing Sheets

U.S. PATENT DOCUMENTS

| | | | |
|---|---|---|---|
| 5,540,713 | A | 7/1996 | Schnepp-Pesch et al. |
| 5,562,697 | A | 10/1996 | Christiansen |
| 5,569,295 | A | 10/1996 | Lam |
| 5,571,166 | A | 11/1996 | Dinh et al. |
| 5,575,816 | A | 11/1996 | Rudnick et al. |
| 5,591,197 | A | 1/1997 | Orth et al. |
| 5,591,224 | A | 1/1997 | Schwartz et al. |
| 5,697,971 | A * | 12/1997 | Fischell et al. ............. 623/1.15 |
| 5,707,387 | A | 1/1998 | Wijay |
| 5,716,396 | A | 2/1998 | Williams, Jr. |
| 5,741,327 | A | 4/1998 | Frantzen |
| 5,800,520 | A | 9/1998 | Fogarty et al. |
| 5,810,872 | A * | 9/1998 | Kanesaka et al. .......... 623/1.15 |
| 5,843,168 | A * | 12/1998 | Dang ........................ 623/1.15 |
| 5,897,588 | A | 4/1999 | Hull et al. ...................... 623/1 |
| 5,911,754 | A * | 6/1999 | Kanesaka et al. ........... 606/198 |
| 5,913,895 | A * | 6/1999 | Burpee et al. .................. 623/1 |
| 5,913,896 | A | 6/1999 | Boyle et al. .................... 623/1 |
| 5,913,897 | A | 6/1999 | Corso, Jr. et al. ............... 623/1 |
| 5,931,866 | A | 8/1999 | Frantzen ........................ 623/1 |
| 5,972,018 | A | 10/1999 | Israel et al. ................. 606/198 |
| 5,980,552 | A * | 11/1999 | Pinchasik et al. .......... 623/1.16 |
| 6,042,597 | A * | 3/2000 | Kveen et al. ............... 623/1.15 |
| 6,312,462 | B1 | 11/2001 | McDermott et al. ........ 623/1.25 |
| 6,395,019 | B2 | 5/2002 | Chobotov .................. 623/1.13 |
| 6,488,703 | B1 * | 12/2002 | Kveen et al. ............... 623/1.15 |

FOREIGN PATENT DOCUMENTS

| | | |
|---|---|---|
| EP | 0 749 729 A2 | 12/1996 |
| EP | 0 945 107 A2 | 9/1999 |
| FR | 2758253 | 7/1998 |
| WO | WO 97/14375 | 4/1997 |
| WO | WO 97/21403 | 6/1997 |
| WO | WO 98/07386 | 2/1998 |
| WO | 98/30173 | 7/1998 |
| WO | 98/40035 | 9/1998 |
| WO | 99/53862 | 10/1999 |

OTHER PUBLICATIONS

Abstract from the PCT Gazette of PCT Patent International Publication No. WO 98/38945, Published Sep. 11, 1998.
Abstract from the PCT Gazette of PCT Patent International Publication No. WO 98/41168, Published Sep. 24, 1998.
Abstract from the PCT Gazette of PCT Patent International Publication No. WO 98/41169, Published Sep. 24, 1998.
Abstract from the PCT Gazette of PCT Patent International Publication No. WO 98/41170, Published Sep. 24, 1998.
RSTENT™ Product Brochure.

* cited by examiner

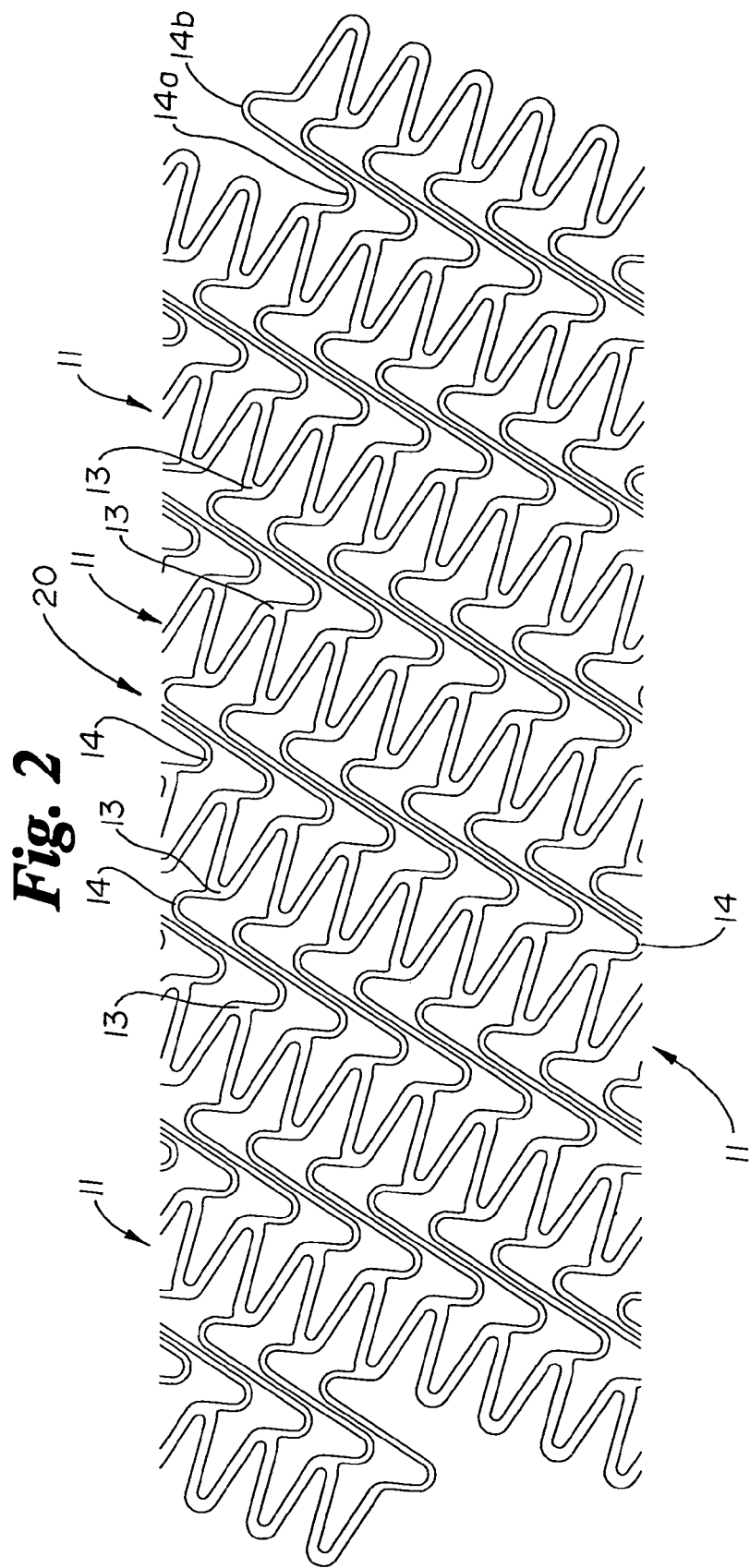

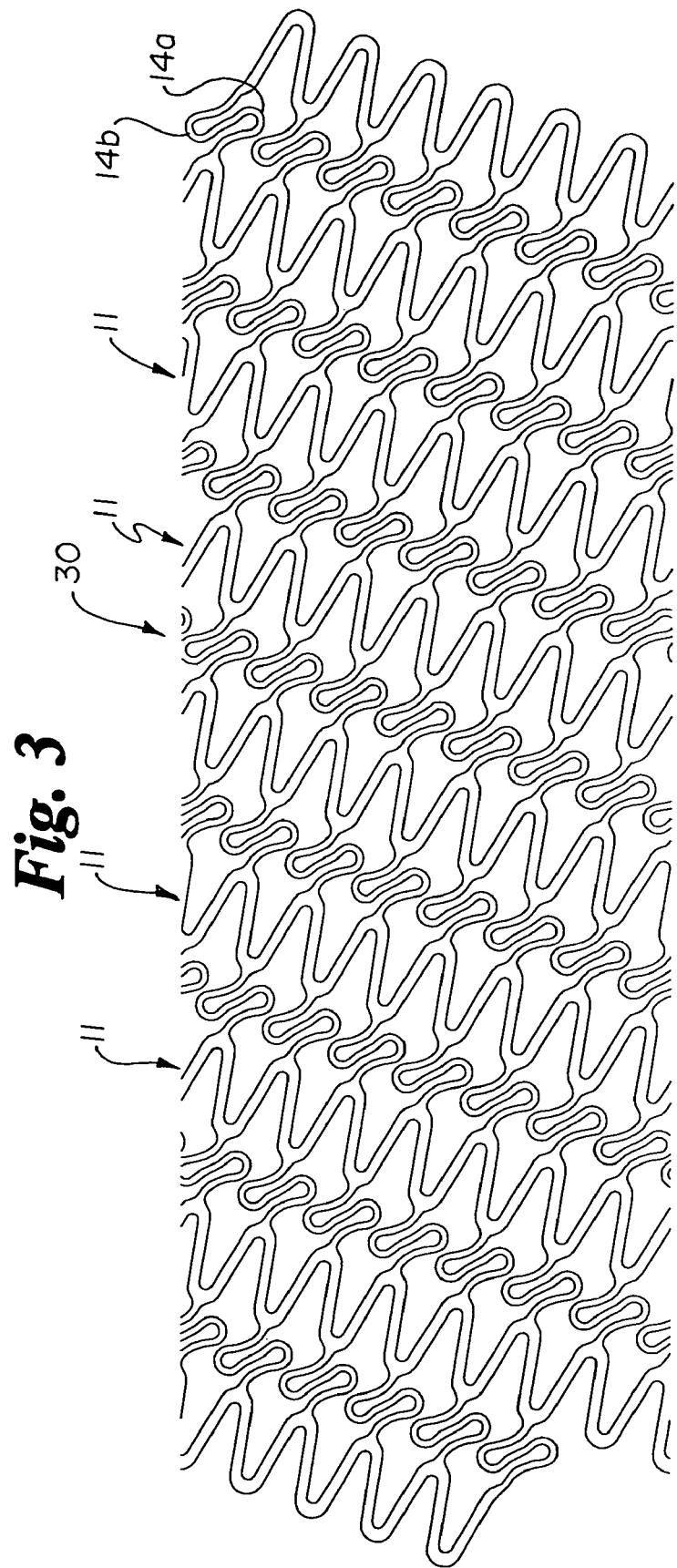

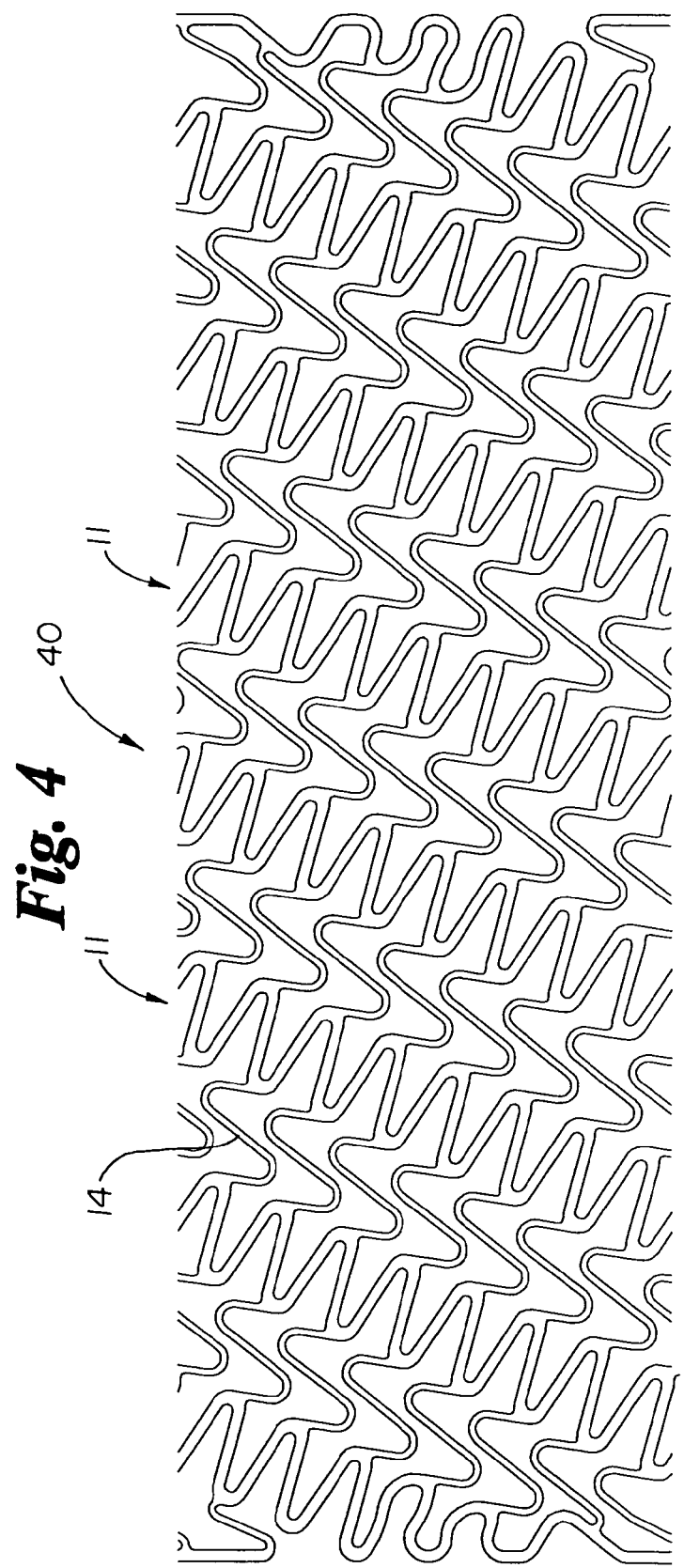

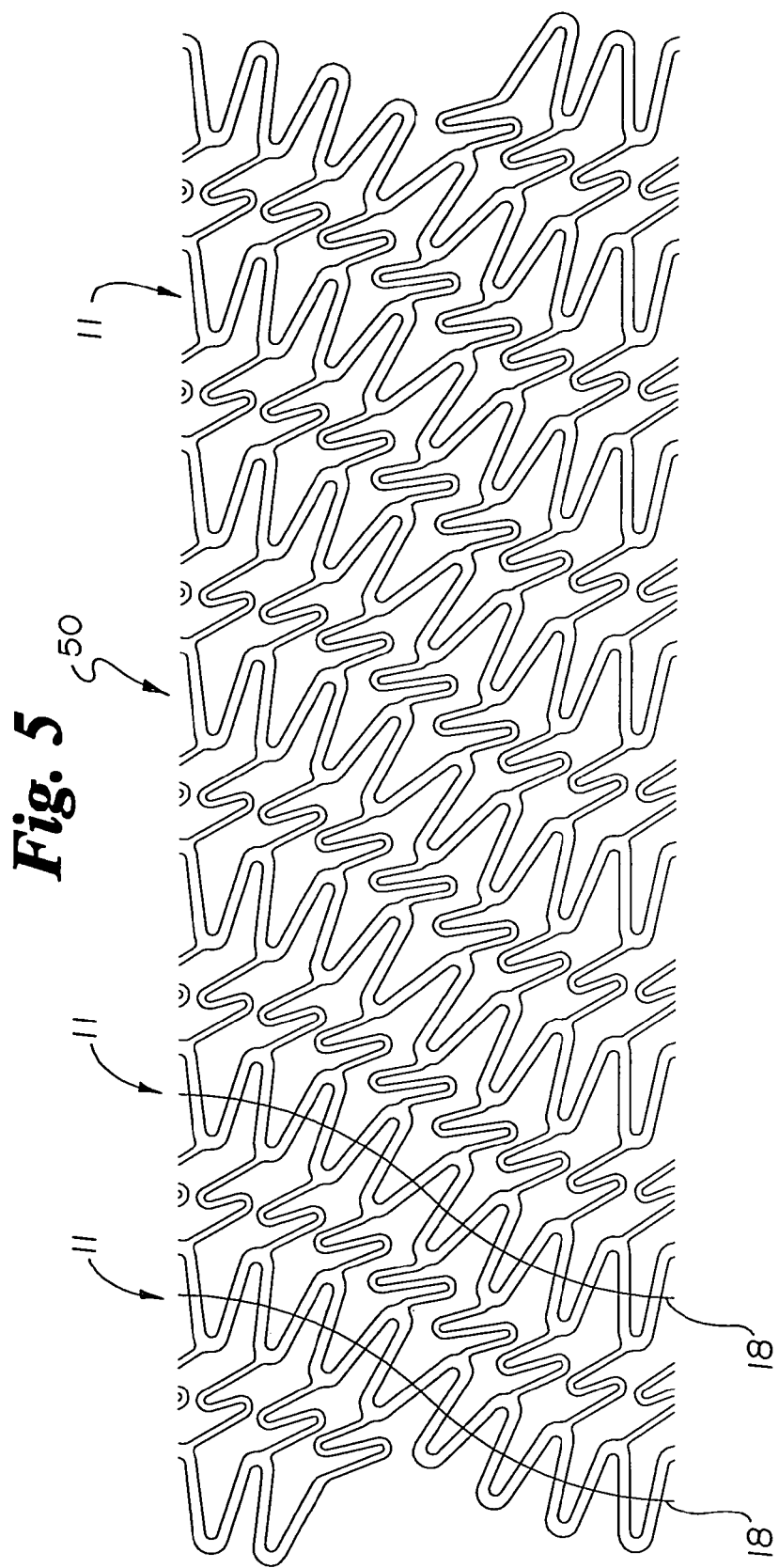

HELICAL STENT DESIGN

CROSS-REFERENCE TO RELATED APPLICATIONS

This application is a continuation of U.S. patent application Ser. No. 10/280,960, filed Oct. 25, 2002, which is a continuation of U.S. patent application Ser. No. 09/537,244, filed Mar. 28, 2000 and which issued as U.S. Pat. No. 6,488,703, which is a continuation of U.S. patent application Ser. No. 09/178,457, filed Oct. 23, 1998, and which issued as U.S. Pat. No. 6,042,597, the entire contents of all of which are incorporated herein by reference.

BACKGROUND OF THE INVENTION

The present invention relates to stents. A stent, generally speaking, is a device that can be placed within a body lumen or interior space for supporting and assuring patency of a lumen. Patency refers to the state of being freely open and is particularly important in the vascular system. The field of angioplasty is concerned with the reconstruction of blood vessels and stents are used, for example, for holding blood vessels open or for back tacking intimal flaps inside the vessels after angioplasty. More generally, however, stents can be used inside the lumina of any physiological conduit including arteries, veins, vessels, the biliary tree, the urinary tract, the elementary tract, the tracheal bronchial tree, the genitourinary system, and the cerebral aqueduct. Stents can be used inside lumina of animals and/or humans.

Stents are generally tubular in structure and are radially expandable between an unexpanded insertion size or circumference and an expanded implantation size or circumference which is greater than the unexpanded insertion size.

An important attribute of a stent is that it be radially compressible and expandable so that it will easily pass through a blood vessel or the like when collapsed and will expand or can be expanded to its implanted size after the implantation location has been reached. It is also desirable that a stent be generally flexible throughout its length so that it is easily maneuverable through bends and curves of the vascular system or the like to reach the implantation site and that the stent be conformable to the vascular site when expanded. It is also typically desirable that a stent have a substantial amount of open space so as to allow for endothelialization along its length to minimize foreign body response and to minimize interference with collateral blood vessels and the like.

There have been introduced various types of stents and various stent designs. Stents are generally categorized as being self-expandable, i.e., which expand by themselves and balloon expandable, i.e., expanded by a balloon inserted inside the stent.

From the view point of materials, stents can be categorized as being made from various metals such as stainless steel, nitinol and from various plastics.

Stents can be made from tubular stock structures from which a desired design may be cut or etched. Also they may be made from wire. Both of these types are well known.

Details of prior art stents can be found in U.S. Pat. Nos. 5,562,697, 5,540,713, 5,575,816, 5,569,295, 5,496,365, 5,344,426, 5,139,480, 5,135,536, 5,810,872, 5,226,913, 5,716,396, and 5,370,683.

This invention relates to all of the above-discussed types of stents and incorporates herein by reference all of the above patents specifically identified herein.

It is an object of the invention to provide, as a preferred embodiment, a stent comprised of a helically wound serpentine or undulating structure including curved connecting elements, i.e., curvilinear, which produces closed flexible cells in the expanded form. In combination the flexible cells yield a flexible, conformable stent which expands uniformly and provides good radial strength, scaffolding and fatigue characteristics when expanded.

Stents incorporating the design of the invention are preferably made from wire windings as in the prior art or from tubes such as metal tubes which are etched or laser cut to obtain the desired configuration of the stent in accordance with the invention.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

BRIEF SUMMARY OF THE INVENTION

Generally speaking the present invention provides a stent comprised of two major structural elements, the first being a continuous elongated helical element preferably comprised of spaced undulating portions forming periodic end loop portions, i.e., a serpentine configuration, the helical element extending substantially over the length of the stent body to create a cylindrical stent configuration. The second element comprises a plurality of curvilinear, most preferably sinusoidal, connectors extending between and interconnecting at least some of the adjacent undulating portions, preferably connected to the end loop portions, of the helical element over its length. A double parallel helix or multiple parallel helices may also be used but the single helix as described hereinbelow is preferred.

BRIEF DESCRIPTION OF THE DRAWINGS

FIG. 2 is a view similar to FIG. 1 of another embodiment of the invention;

FIG. 3 is a similar view according to a third embodiment of the invention;

FIG. 4 is again a similar view of yet another embodiment of the invention;

FIG. 5 is a similar view of a further embodiment of the invention;

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
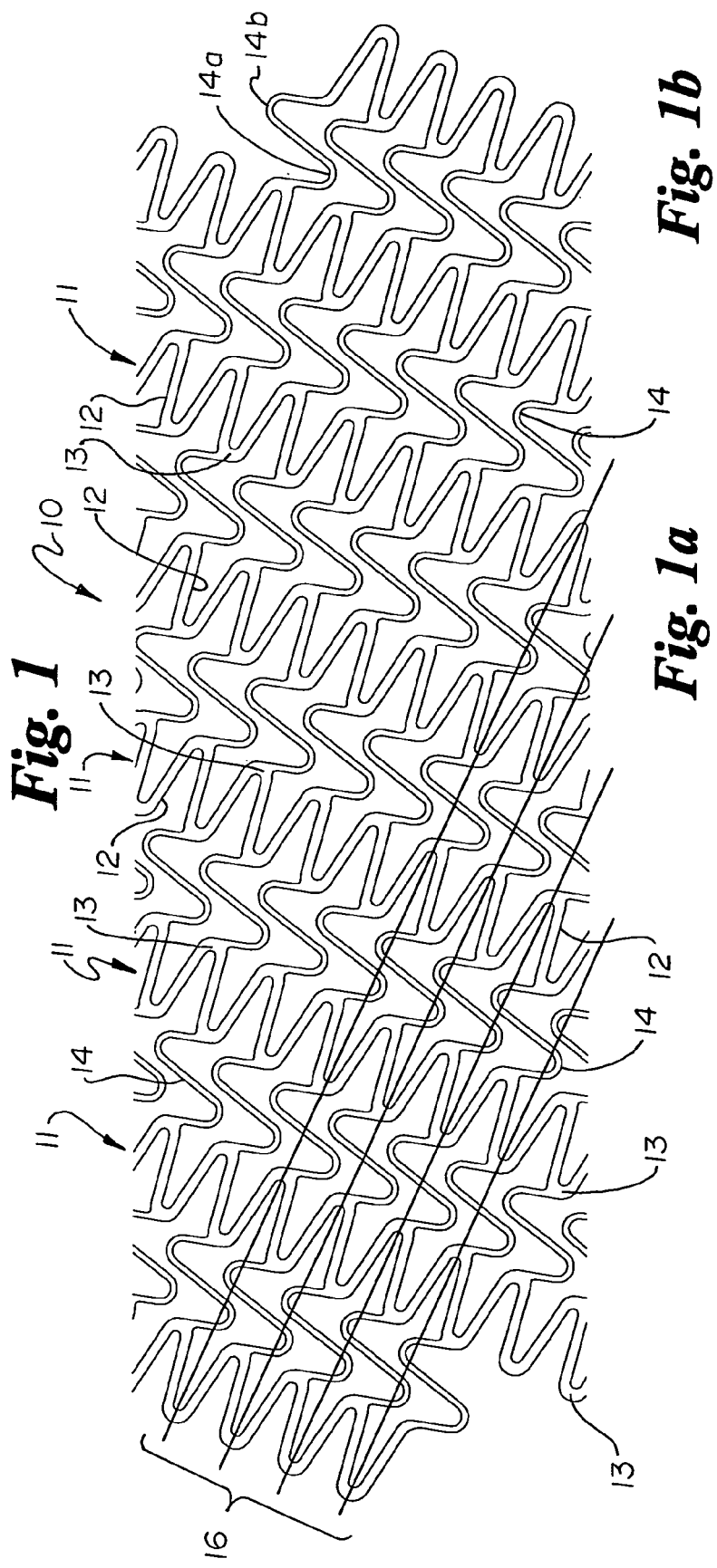
FIG. 1 is a side view of a stent extended in a flat form according to a first embodiment of the invention.

A stent 10 of a first embodiment the invention as shown in FIG. 1. The stent 10 is formed of a diagonally arranged helical band 11 which is arranged spirally in a cylindrical shape. The band 11 includes undulating portions 12 over its entire continuous length to provide a serpentine configuration. As can be seen in the Figure, each of the undulating portions includes loop end portions 13. Each loop end portion 13 is interconnected with an adjacent longitudinally spaced end portion 13 by a curvilinear connector element 14 which, in this embodiment, includes two bends or U-shaped portions 14a and 14b to form a connector having a preferred sinusoidal shape. Also as can be seen from FIG. 1 in this embodiment the interconnecting elements 14 preferably join end portions 13 at their extreme ends and extend directly between longitudinally spaced adjacent end portions. The connectors may be attached to other locations on the undulations other than the extreme ends. Also, with respect to the stent of FIG. 1, it should be noted that the undulations are out of phase as indicated by lines 16.

In this embodiment as in all of the embodiments disclosed, the stent is preferably formed from a tubular stock material by laser cutting. However, a tube may be etched as well. It is possible to form a desired configuration from flat sheet stock which is then bent into the desired cylindrical configuration. This is a procedure which is know in the art.

Figure 1B:
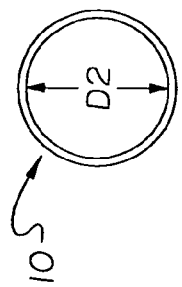
FIG. 1b is a front view of a stent after it is expanded.
Figure 1A:
FIG. 1a is a front view of a stent before it is expanded.

When a stent such as that shown in FIG. 1 is implanted in a body lumen, such as an artery, with the stent having an initial diameter $D_1$ as shown in FIG. 1a as delivered into the lumen to the desired location, the stent can be flexed and bent easily in a meandering lumen during delivery. Then, the stent is expanded to have a second diameter $D_2$ as shown in FIG. 1b which is larger than the initial diameter $D_1$ whereby the stent is implanted.

When the stent is delivered and expanded, a delivery catheter assembly with an expandable member, such as a balloon, is preferably used as is know in the art. When the catheter assembly with a balloon is used to deliver the stent, the stent is mounted on the balloon and the catheter assembly is pushed into the implantation site. Then, the balloon is inflated, radially applying a force inside the stent and the stent is expanded to its expanded diameter.

Referring now to FIG. 2, a second embodiment of the invention is shown which is similar in most respects to the embodiment shown in FIG. 1 with the exception that the sinusoidal connector elements 14 extend between end portions 13 which are not only longitudinally adjacent but are spaced upwardly or downwardly with respect to each other. Again, the serpentine configuration is out of phase.

Referring now to FIG. 3, another embodiment of the invention is shown which is comprised of similar undulating structural elements 11 as is described with reference to FIGS. 1 and 2. However, in this embodiment the connecting elements 14 are of a different configuration in the sense that the two U-shaped bends 14a and 14b are closer together, the resulting configuration not being strictly speaking "sinusoidal" but being curvilinear.

Other curvilinear configurations may also be used for the connector elements. For example, spiral configurations may be used such as those disclosed in U.S. patent application Ser. No. 08/846,164 filed Apr. 25, 1997, entitled "Improved Stent Configurations Including Spirals", which application is incorporated herein by reference in its entirety.

Referring now to the embodiment of FIG. 4, it can be seen that this embodiment is also somewhat similar to that of FIG. 1. However, in this embodiment the ends of the stent rather than being diagonal as shown in FIG. 1 are squared off with respect to the longitudinal axis of the stent 40.

Referring now to FIG. 5, another embodiment of a stent 50 according to this invention is shown. Again, the basic elements of this stent are similar to those of the preceding embodiments with the exception that the helical elements 11 are not merely diagonal in arrangement but are curvilinear as well. This is demonstrated by reference to lines 18.

Figure 6:
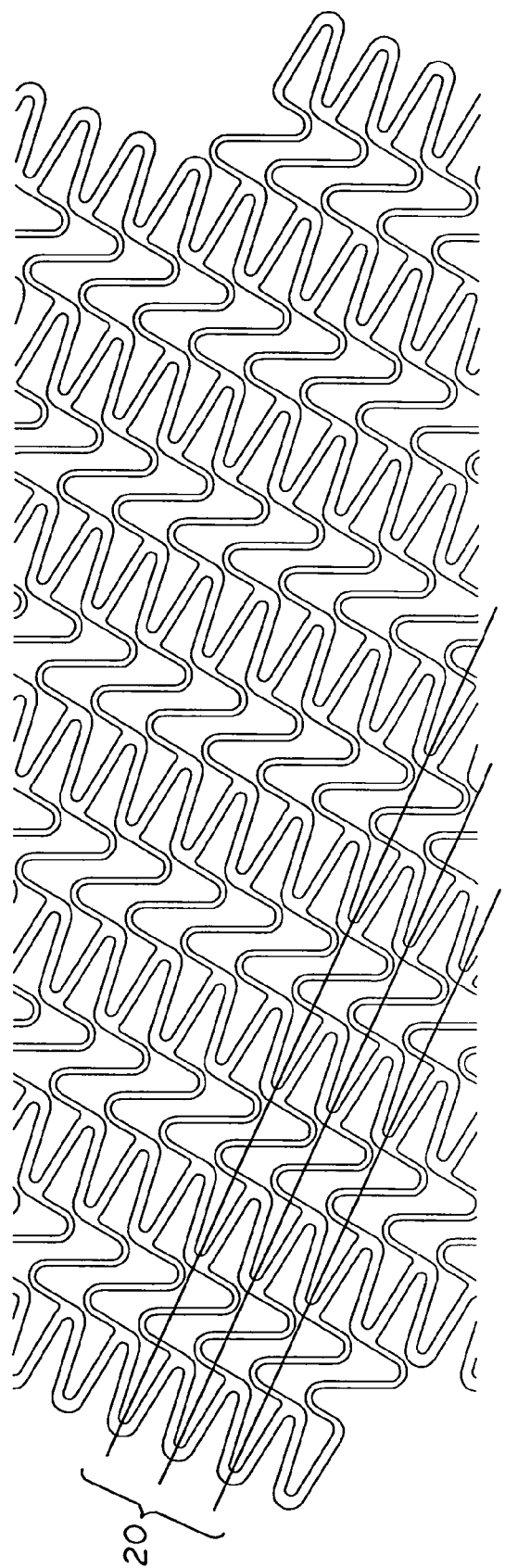
FIG. 6 is a similar view of still another embodiment of the invention.

Referring now to the embodiment shown in FIG. 6, it can be seen that the undulations of the helical element 11 can be arranged so as to be in phase as is shown by lines 20.

Figure 7:
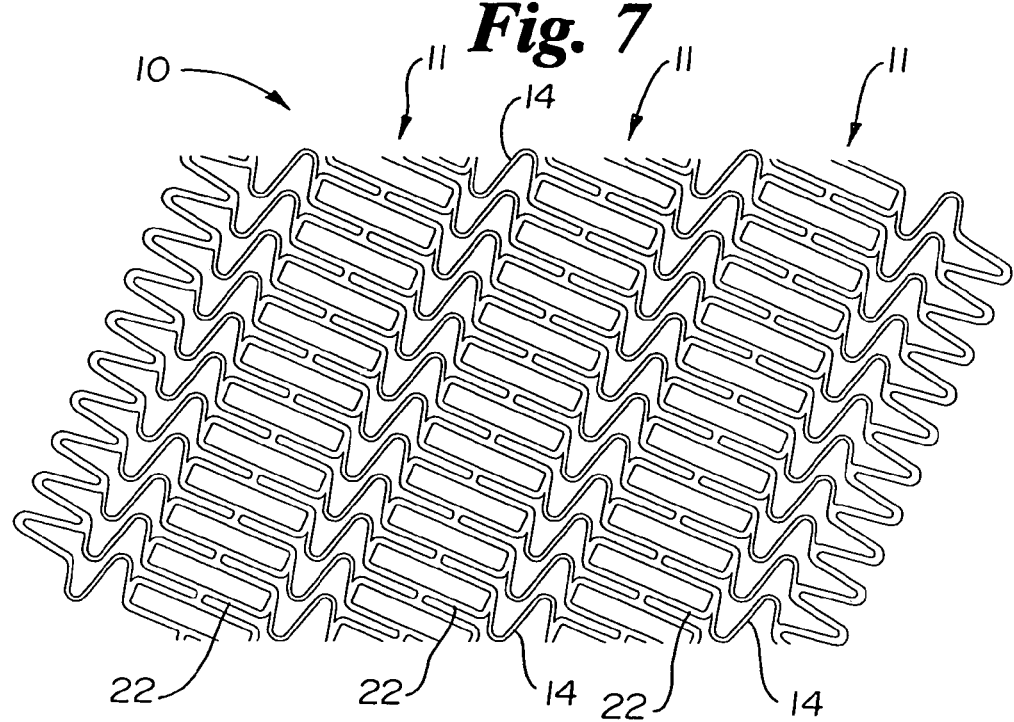
FIG. 7 is a fragmentary flat form view of another stent embodiment.
Figure 8:
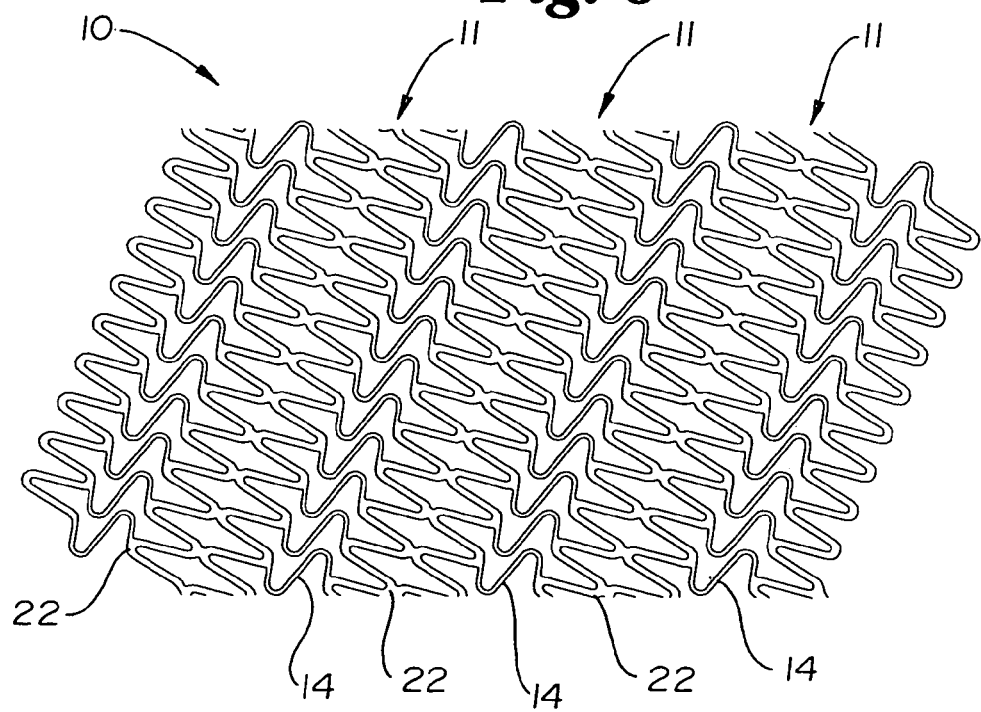
FIG. 8 is a fragmentary flat form view of yet another stent embodiment.
Figure 9:
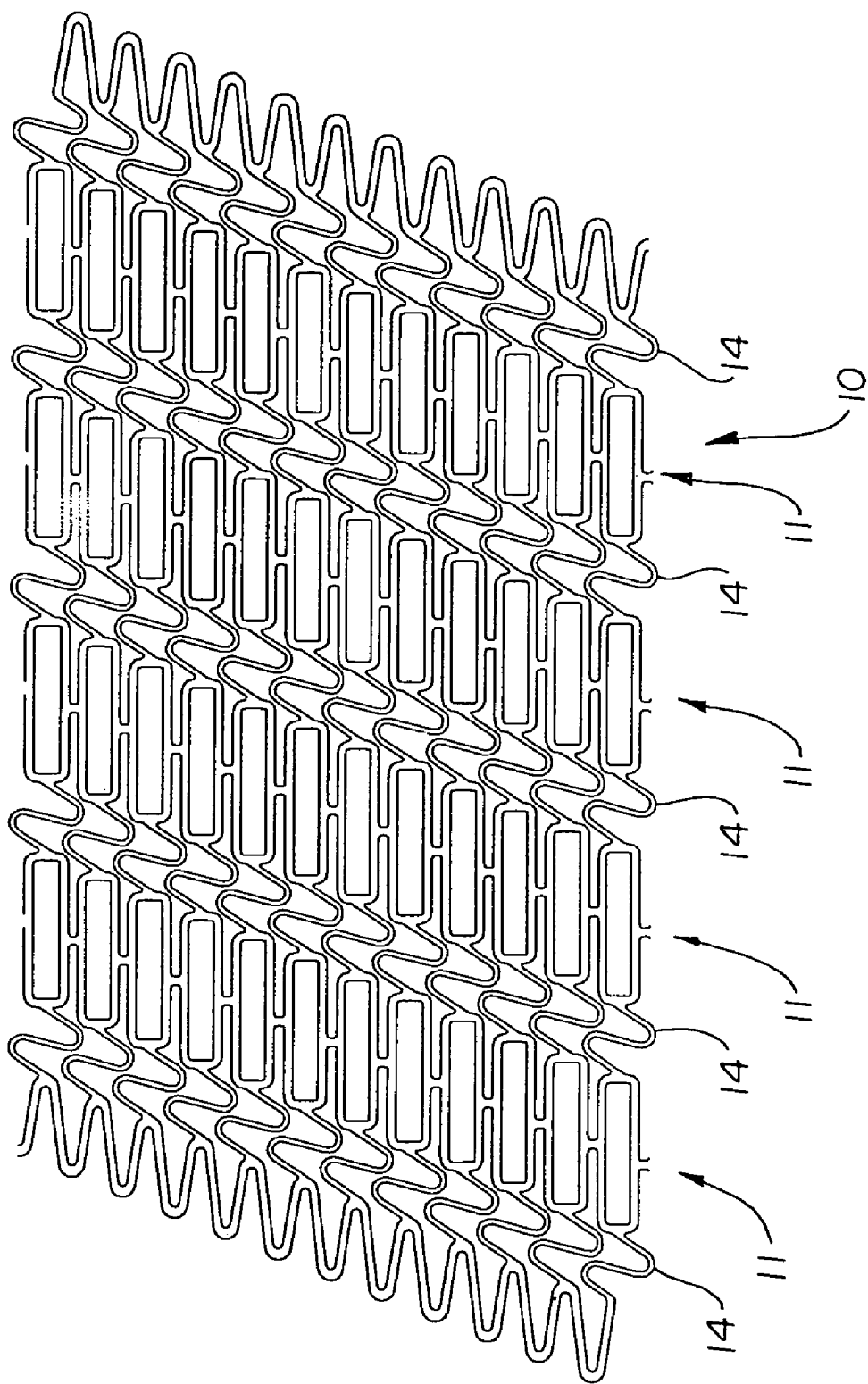
FIG. 9 is a fragmentary flat form view of another stent embodiment.

Referring now to FIGS. 7, 8 and 9, a fragment of a stent 10 is shown in each Figure including helical bands 11. In FIGS. 7 and 9 the bands are made up of interconnected rectangular cells and in FIG. 8 the cells are joined serpentine or diamond shaped cells. In these Figures the curvilinear connector elements 14 are the preferred sinusoidal configuration.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A tubular stent, the tubular stent having a length, the tubular stent comprising:
    at least one continuous elongated helical band element extending substantially over the length of the tubular stent, the helical band element having a plurality of interconnected loop portions, and a curvilinear midline, the midline extending midway between loop portions of the elongated helical band element.

2. The stent of claim 1 wherein a plurality of curvilinear elements extends between and interconnects loops of adjacent turns of the helical element.

3. The stent of claim 2 in which adjacent curvilinear elements have different orientations relative to the longitudinal axis of the stent.

4. The stent of claim 2 in which the curvilinear elements include at least two bends.

5. The stent of claim 4 in which the bends open in substantially opposite directions.

6. The stent of claim 2 in which the curvilinear elements have spiral configurations.

7. The stent of claim 1 in which the interconnected loop portions are in a sinusoidal pattern.

8. A stent having a longitudinal axis, the stent comprising a helical band element which extends for a plurality of turns about the longitudinal axis, the stent having a plurality of undulating portions forming alternating peaks and troughs, peaks from one turn of the helical band element connected to troughs of an adjacent turn of the helical band element via curvilinear elements, the helical band element undulating about a curvilinear midline.

9. The stent of claim 8 wherein one or more of the undulating portions are disposed at different oblique angles, relative to one another, relating to the longitudinal axis throughout the helical band.

10. The stent of claim 8 in which the undulating portions are in a sinusoidal pattern.

11. The stent of claim 8 in which the curvilinear elements include at least two bends.

12. The stent of claim 8 in which the curvilinear elements have spiral configurations.

13. In combination, a delivery catheter comprising a balloon with a tubular stent disposed thereabout, the stent having a length and comprising:

at least one continuous elongated helical band element extending substantially over the length of the tubular stent, the helical band element having a plurality of interconnected loop portions, and a curvilinear midline, the midline extending midway between loop portions of the elongated helical band element.

14. The combination of claim 13 wherein a plurality of curvilinear elements extends between and interconnects loops of adjacent turns of the helical element.

15. The combination of claim 14 in which adjacent curvilinear elements have different orientations relative to the longitudinal axis of the stent.

16. The combination of claim 14 in which the curvilinear elements include at least two bends.

17. The combination of claim 16 in which the bends open in substantially opposite directions.

18. The combination of claim 14 in which the curvilinear elements have spiral configurations.

19. The combination of claim 13 in which the interconnected loop portions are in a sinusoidal pattern.

20. A tubular stent, the tubular stent having a length and a longitudinal axis, the tubular stent comprising a continuous elongated band element spiraling about the longitudinal axis of the stent and extending substantially over the length of the tubular stent, the band element having a width, the width defined by a first curvilinear spiral line and a second curvilinear spiral line, the band element comprising a first plurality of loop end portions and a second plurality of loop end portions, a tip of each of the first plurality of loop end portions being positioned on the first curvilinear spiral line and a tip of each of the second plurality of loop end portions being positioned on the second curvilinear spiral line.

21. A tubular stent, the tubular stent having a length, the tubular stent comprising:

at least one continuous elongated helical band element extending substantially over the length of the tubular stent and connectors connecting adjacent turns of the helical band element, the helical band element having a plurality of interconnected loop portions which define an envelope, the envelope of the helical band like element having a non-constant pitch, and the connectors having an elongated portion at either end and an elongated middle portion, each of the elongated end portions connected to the elongated middle portion via a bent portion.

* * * * *